US012678200B2

(12) United States Patent
Kaiser et al.

(10) Patent No.: US 12,678,200 B2
(45) Date of Patent: Jul. 14, 2026

(54) CRANIAL FIXATION DEVICES

(71) Applicant: Rensselaer Polytechnic Institute, Troy, NY (US)

(72) Inventors: Luke Douglas Kaiser, Greenwich, CT (US); Max Phoenix, Pepperell, MA (US); John Lurie, New York, NY (US); Akanksha Singh, Apex, NC (US); Mousa Hamad, Clifton, NJ (US)

(73) Assignee: Rensselaer Polytechnic Institute, Troy, NY (US)

( * ) Notice: Subject to any disclaimer, the term of this patent is extended or adjusted under 35 U.S.C. 154(b) by 51 days.

(21) Appl. No.: 18/381,250

(22) Filed: Oct. 18, 2023

(65) Prior Publication Data

US 2024/0122626 A1 Apr. 18, 2024

Related U.S. Application Data

(60) Provisional application No. 63/417,012, filed on Oct. 18, 2022.

(51) Int. Cl.
*A61B 17/68* (2006.01)
*A61F 2/28* (2006.01)
(52) U.S. Cl.
CPC .......... *A61B 17/688* (2013.01); *A61F 2/2875* (2013.01)
(58) Field of Classification Search
CPC . A61B 17/68; A61B 2017/681; A61B 17/688; A61F 2/2875
USPC .......................................................... 606/60
See application file for complete search history.

(56) References Cited

U.S. PATENT DOCUMENTS

| | | | | |
|---|---|---|---|---|
| 5,707,373 A * | 1/1998 | Sevrain | ................ | A61B 17/688 |
| | | | | 411/338 |
| 6,126,663 A * | 10/2000 | Hair | .................... | A61B 17/688 |
| | | | | 606/324 |
| 6,258,091 B1 * | 7/2001 | Sevrain | ................ | A61B 17/688 |
| | | | | 606/301 |
| 6,328,743 B2 * | 12/2001 | Lerch | .................. | A61B 17/688 |
| | | | | 606/215 |

(Continued)

FOREIGN PATENT DOCUMENTS

| | | |
|---|---|---|
| CN | 104825151 A | 8/2015 |
| CN | 106901883 A | 6/2017 |

(Continued)

*Primary Examiner* — Eduardo C Robert
*Assistant Examiner* — Christina NegrelliRodriguez
(74) *Attorney, Agent, or Firm* — Barclay Damon LLP; Anthony P. Gangemi

(57) ABSTRACT

A fixation device includes a body having a first axial end and a second axial end defining a longitudinal axis. The body has a longitudinal bore therein, and a longitudinal slot in a first side of the body extending laterally to the bore. A mounting bracket is connected to the first axial end at a second side opposite the slot and extends outward therefrom. The mounting bracket is configured to be mounted to a first structure. A support member is retained in the bore and is configured to move longitudinally in the bore. The support member protrudes outward from the first side of the body to support a second structure a longitudinal distance from the first structure. A lead screw engages a threaded hole in the base whereby rotation of the lead screw moves the support member to adjust the longitudinal distance between the first and second structures.

20 Claims, 6 Drawing Sheets

(56) References Cited

U.S. PATENT DOCUMENTS

| | | | |
|---|---|---|---|
| 8,206,425 | B2 | 6/2012 | Khanna |
| 9,468,703 | B2 | 10/2016 | Khanna |
| 9,549,819 | B1 | 1/2017 | Bravo et al. |
| 10,610,378 | B2 | 4/2020 | Piron et al. |
| 2008/0039837 | A1* | 2/2008 | Gambale .............. A61C 8/0018 |
| | | | 606/326 |
| 2020/0197118 | A1* | 6/2020 | Sikander ........... A61B 17/8866 |

FOREIGN PATENT DOCUMENTS

| | | | |
|---|---|---|---|
| CN | 209661974 U | 11/2019 | |
| WO | 2011139839 A1 | 11/2011 | |

* cited by examiner

<u>100</u>

170

172

170

172

174

300

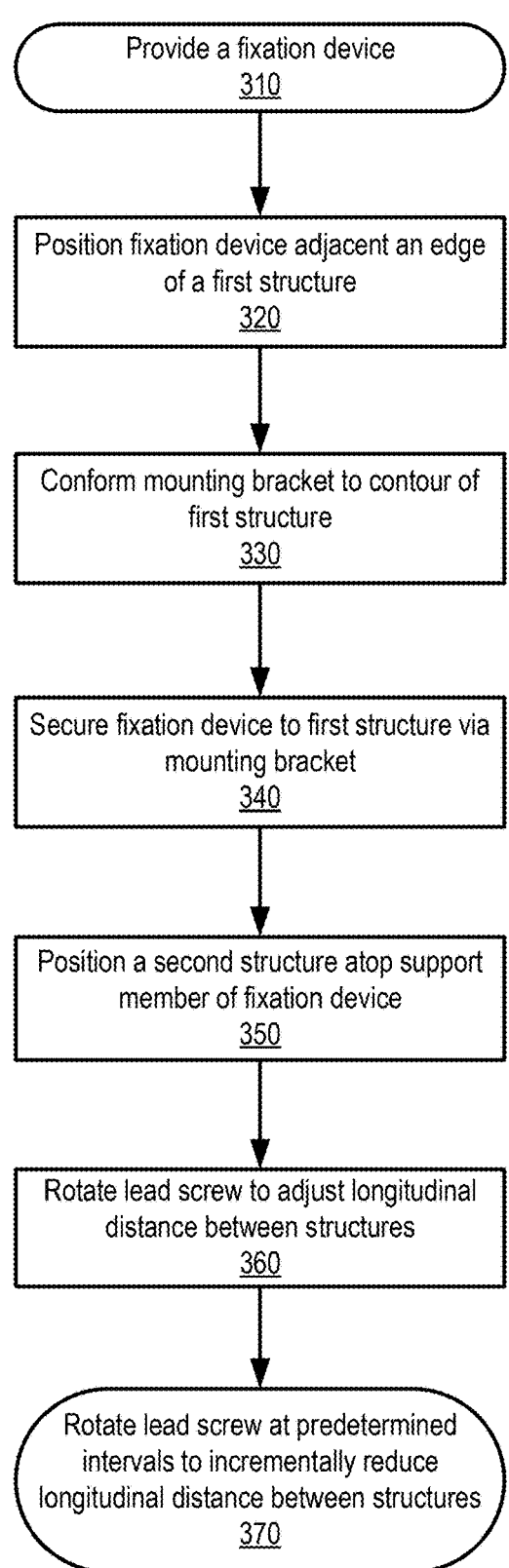

Provide a fixation device
310

Position fixation device adjacent an edge
of a first structure
320

Conform mounting bracket to contour of
first structure
330

Secure fixation device to first structure via
mounting bracket
340

Position a second structure atop support
member of fixation device
350

Rotate lead screw to adjust longitudinal
distance between structures
360

Rotate lead screw at predetermined
intervals to incrementally reduce
longitudinal distance between structures
370

FIG. 9

CRANIAL FIXATION DEVICES

CROSS REFERENCE TO RELATED APPLICATIONS

This application claims the priority benefit of U.S. Provisional Patent Application No. 63/417,012, filed Oct. 18, 2022, the contents of which is incorporated by reference as if disclosed herein in its entirety.

FIELD

The present technology relates generally to bone fixation devices, and more particularly, to cranial fixation devices and for use after craniectomy to improve patient outcomes and quality of life.

BACKGROUND

Following brain trauma (such as stroke, edema, force, etc.), tissue damage to the brain occurs. This tissue damage can result in catastrophic damage to the blood brain barrier, allowing unregulated water uptake from the blood into the brain tissue. This results in swelling of the brain, and elevated intracranial pressure ("ICP"). If left untreated, an elevated ICP crisis can result in mortality. Currently, treatment consists of craniectomy, closure of surgical site and healing without a complete skull, and cranioplasty. However, these two major procedures, craniectomy and cranioplasty, can introduce risk of surgical site infection and complications, as well as cost.

What is needed, therefore, are improved cranial fixation devices that address at least the problems described above.

SUMMARY

According to an embodiment of the present technology, a fixation device is provided. The fixation device includes a body that has a first axial end and a second axial end that define a longitudinal axis of the fixation device. The body has a bore therein that extends longitudinally from the first axial end toward the second axial end, and a slot in a first side of the body. The slot extends longitudinally from the first axial end toward the second axial end and laterally from the first side of the body to the bore. A mounting bracket is connected to the first axial end of the body at a second side that is opposite the slot. The mounting bracket has a proximal end that is connected to the first axial end of the body and a distal end that extends outward from the second side of the body. The distal end of the mounting bracket is configured to be mounted to a first structure. A support member is retained in the bore of the body and is configured to move longitudinally in the bore. The support member has a base that is retained in the bore and an arm that extends from a first side of the base through the slot such that the arm protrudes outward from the first side of the body. The arm is configured to support and position a second structure a longitudinal distance from the first structure. A lead screw is configured to engage a threaded hole in the base of the support member to retain the support member in the bore whereby rotation of the lead screw moves the support member longitudinally in the bore to adjust the longitudinal distance of the second structure from the first structure.

In some embodiments, the arm of the support member includes a proximal end that is connected to the first side of the base, a distal end that has a support surface that is configured to support the second structure, and an intermediate section that connects the proximal end and the distal end. The intermediate section has at least one curved portion such that the proximal end and the distal end are at different positions along the longitudinal axis.

In some embodiments, the intermediate section of the support member includes an upper concave curved portion adjacent to the proximal end and an upper convex curved portion adjacent to the distal end such that the distal end is positioned above the proximal end along the longitudinal axis.

In some embodiments, the intermediate section of the support member includes an upper convex curved portion adjacent to the proximal end and an upper concave curved portion adjacent to the distal end such that the distal end is positioned below the proximal end along the longitudinal axis.

In some embodiments, the bore includes at least one longitudinal groove that is configured to retain a tab of the base of the support member.

In some embodiments, a cap is connected to the first axial end of the body. The cap has a lateral notch that is configured to receive the lead screw.

In some embodiments, the body has a generally cylindrical shape and is configured to be received in a burr hole that separates the first structure and the second structure.

In some embodiments, the first structure is a skull and the second structure is a bone flap that has been removed from the skull or a protective covering that is positioned over an opening in the skull.

In some embodiments, the mounting bracket is configured to conform to a contour of the first structure.

In some embodiments, the distal end of the mounting bracket includes at least one mounting hole that is configured to receive a fastener for mounting the fixation device to the first structure.

According to another embodiment of the present technology, a method of adjustably fixing a first structure to a second structure is provided. The method includes providing a fixation device includes a body having a first axial end and a second axial end defining a longitudinal axis of the fixation device, the body having a bore therein extending longitudinally from the first axial end toward the second axial end and a slot in a first side of the body, the slot extending longitudinally from the first axial end toward the second axial end and laterally from the first side of the body to the bore; a mounting bracket connected to the first axial end of the body at a second side opposite the slot, the mounting bracket having a proximal end connected to the first axial end of the body and a distal end extending outward from the second side of the body, the distal end having at least one mounting hole therein; a support member retained in the bore and configured to move longitudinally in the bore, the support member having a base retained in the bore and an arm extending from a first side of the base through the slot such that the arm protrudes outward from the first side of the body; and a lead screw configured to engage a threaded hole in the base of the support member to retain the support member in the bore whereby rotation of the lead screw moves the support member longitudinally in the bore; positioning the body of the fixation device adjacent an edge of the first structure such that the distal end of the mounting bracket is atop the first structure; inserting a fastener through each of the at least one mounting holes of the mounting bracket to secure the fixation device to the first structure; positioning a bottom surface of the second structure atop the arm of the support member; and rotating the lead screw to adjust a longitudinal distance between the first structure and the second structure.

In some embodiments, the method further includes conforming the mounting bracket to a contour of the first structure.

In some embodiments, the method further includes rotating, at predetermined intervals, the lead screw to incrementally reduce the longitudinal distance between the first structure and the second structure.

According to another embodiment of the present technology, a system of adjustably fixing a first structure to a second structure is provided. The system includes a first structure, a second structure, and at least one burr hole separating the first structure and the second structure. A fixation device is positioned in each of the at least one burr holes. Each fixation device includes a body that has a first axial end and a second axial end that define a longitudinal axis of the fixation device. The body has a bore therein that extends longitudinally from the first axial end toward the second axial end, and a slot in a first side of the body. The slot extends longitudinally from the first axial end toward the second axial end and laterally from the first side of the body to the bore. A mounting bracket is connected to the first axial end of the body at a second side that is opposite the slot. The mounting bracket has a proximal end that is connected to the first axial end of the body and a distal end that extends outward from the second side of the body. The distal end of the mounting bracket is configured to be mounted to the first structure. A support member is retained in the bore of the body and is configured to move longitudinally in the bore. The support member has a base that is retained in the bore and an arm that extends from a first side of the base through the slot such that the arm protrudes outward from the first side of the body. The arm is configured to support and position the second structure a longitudinal distance from the first structure. A lead screw is configured to engage a threaded hole in the base of the support member to retain the support member in the bore whereby rotation of the lead screw moves the support member longitudinally in the bore to adjust the longitudinal distance of the second structure from the first structure.

Further objects, aspects, features, and embodiments of the present technology will be apparent from the drawing Figures and below description.

BRIEF DESCRIPTION OF DRAWINGS

Some embodiments of the present technology are illustrated as an example and are not limited by the figures of the accompanying drawings, in which like references may indicate similar elements.

FIG. 9 is a flowchart outlining the steps of a method for adjustably fixing a first structure to a second structure according to some embodiments of the present technology.

DETAILED DESCRIPTION

Figure 1A:
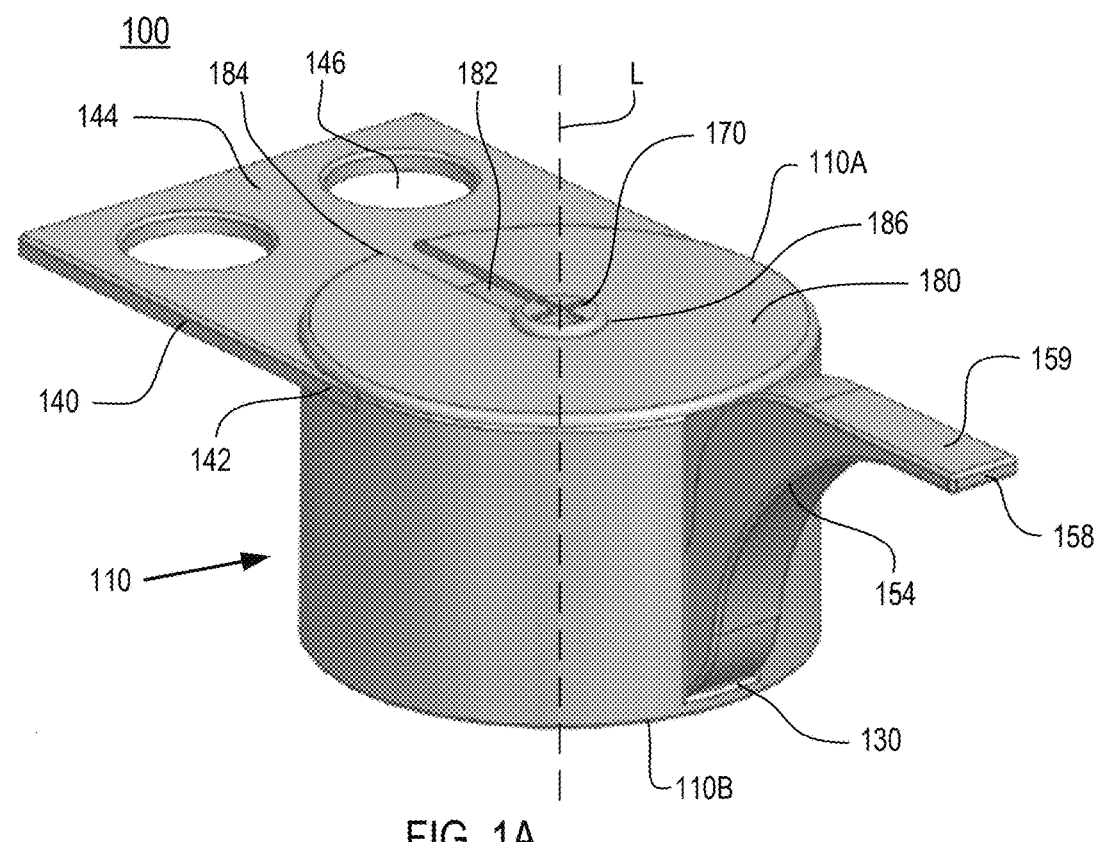
FIG. 1A is an isometric view of a cranial fixation device according to some embodiments of the present technology.
Figure 1B:
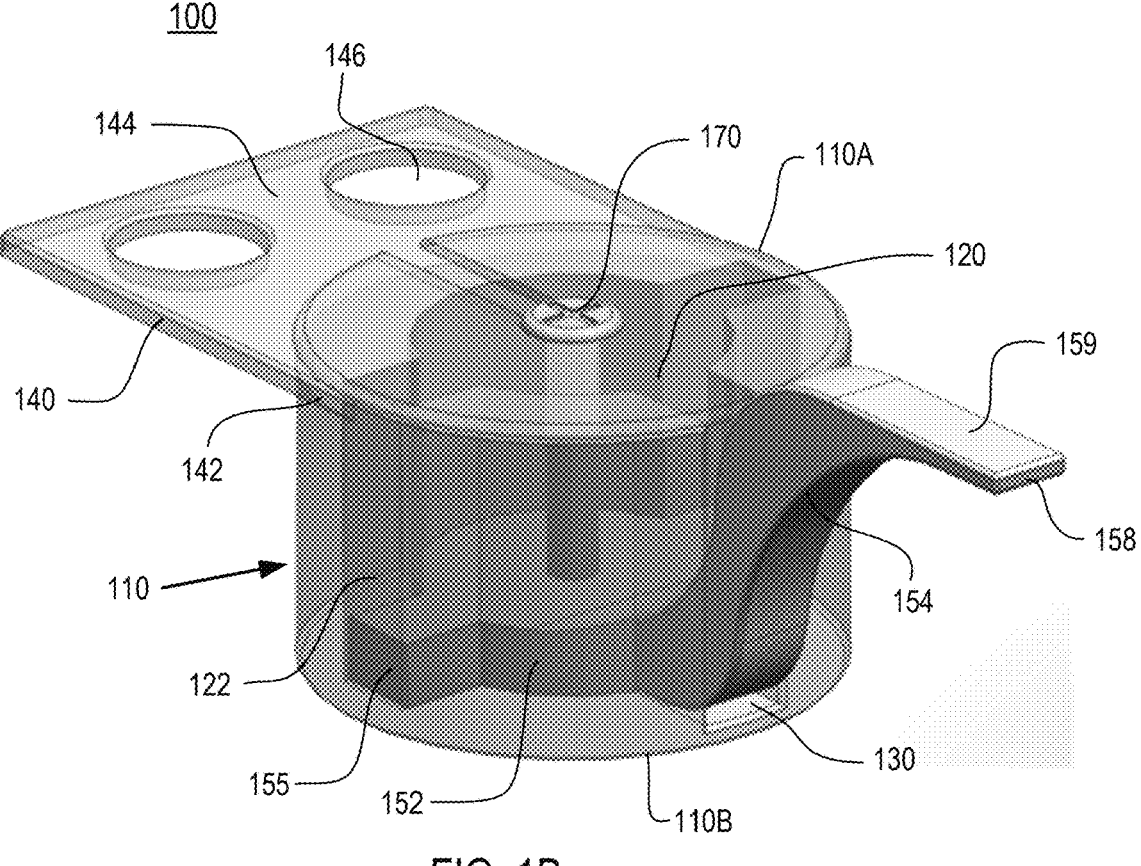
FIG. 1B is an isometric partially exposed view showing the internal components of the cranial fixation device of FIG. 1A.
Figure 2:
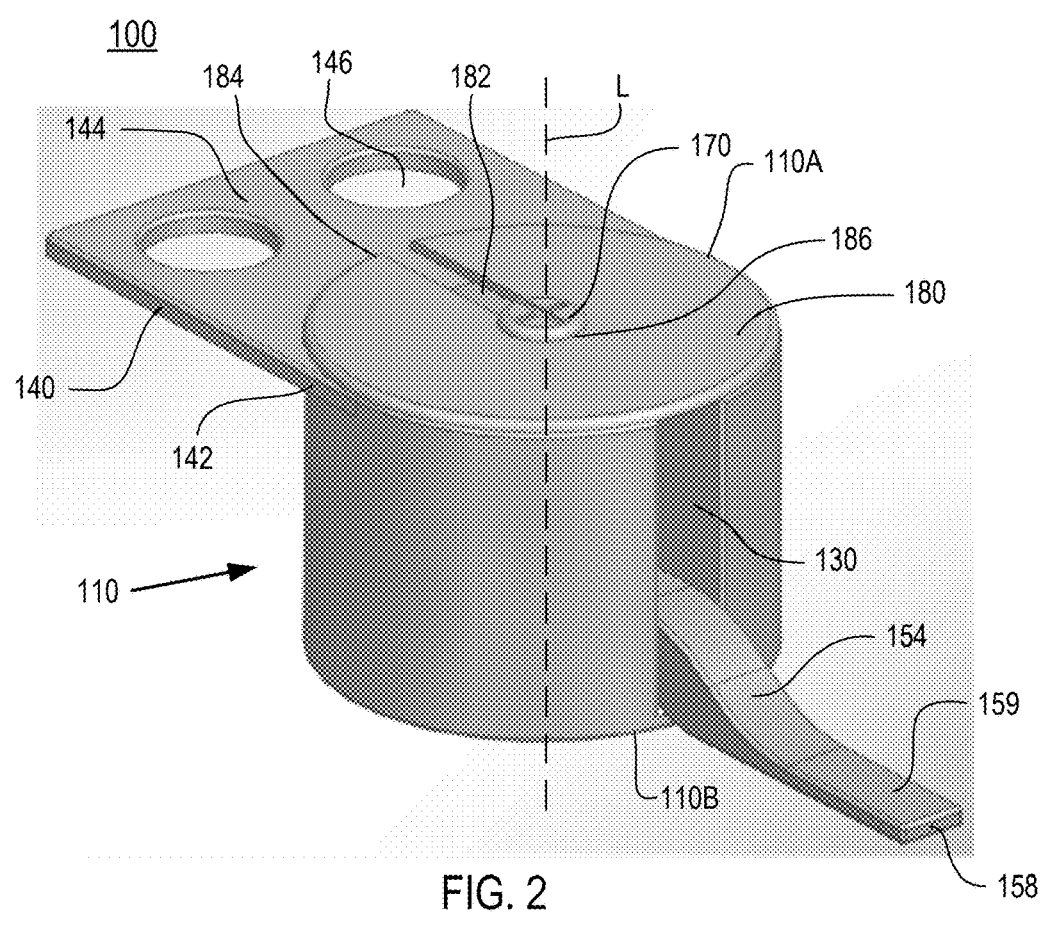
FIG. 2 is an isometric view of a cranial fixation device according to some embodiments of the present technology.

As shown in FIGS. 1A-2, a cranial fixation device is generally designated by the numeral 100. The device 100 has a body 110 that has a first axial end 110A and a second axial end 110B that define a longitudinal axis L of the device 100. In some embodiments, the body 110 is generally cylindrically shaped such that the body 110 is configured to be positioned in a hole separating two structures, such as a burr hole in the skull of a craniectomy patient. However, the present technology is not limited thereto and contemplates embodiments where the body 110 is differently shaped.

Figure 3:
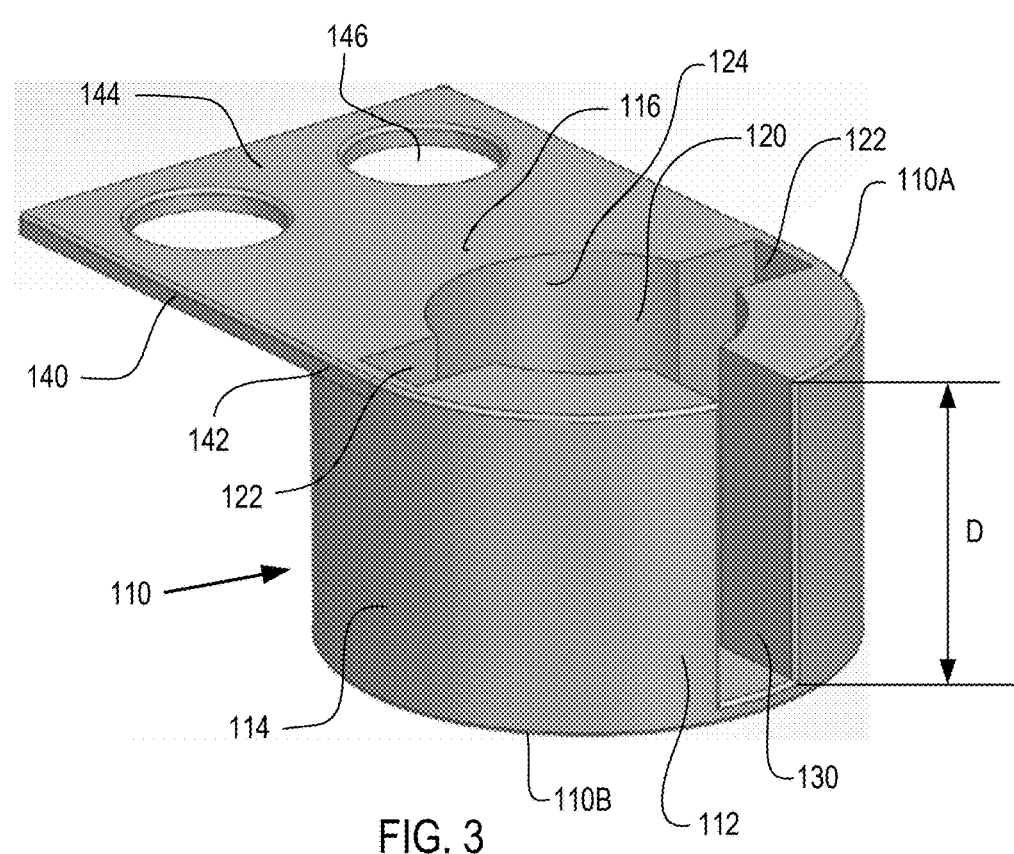
FIG. 3 is an isometric view of a body of a cranial fixation device according to some embodiments of the present technology.

As shown in FIG. 3, the body 110 has a bore 120 therein that extends longitudinally (i.e., along the longitudinal axis L) from the first axial end 110A toward the second axial end 110B such that the bore 120 does not pass all the way through the body 110. A slot 130 extends longitudinally from the first axial end 110A toward the second axial end 110B such that the slot 130 does not pass all the way through the body 110 and has a depth D that is equal to the depth of the bore 120. The slot 130 extends laterally (i.e., generally perpendicularly to the longitudinal axis L) from a first side of the body 112 to the bore 120 such that the slot 130 provides exterior access to the bore 120. In some embodiments, the bore 120 has at least one groove 122 that extends longitudinally the depth of the bore 120. The groove 122 extends laterally from an interior wall 124 that defines the bore 120 toward an exterior wall 114 of the body 110 such that the groove 122 does not pass all the way through the body 110 laterally (i.e., the groove 122 does not provide exterior access to the bore 120). In some embodiments, the bore 120 includes two opposing grooves 122 that are each generally perpendicular to the slot 130. However, the present technology is not limited thereto and contemplates embodiments where the bore 120 includes any number of grooves 122 in any arrangement. In some embodiments, the bore 120 has a generally cylindrical shape such that the grooves 122 and the slot 130 extend radially outward therefrom. However, the present technology is not limited thereto and contemplates embodiments where the bore 120 is differently shaped. In some embodiments, the body 110 is formed of a metal material, such a titanium alloy (e.g., Ti-6AL-4V Grade 5 titanium alloy).

Figure 8A:
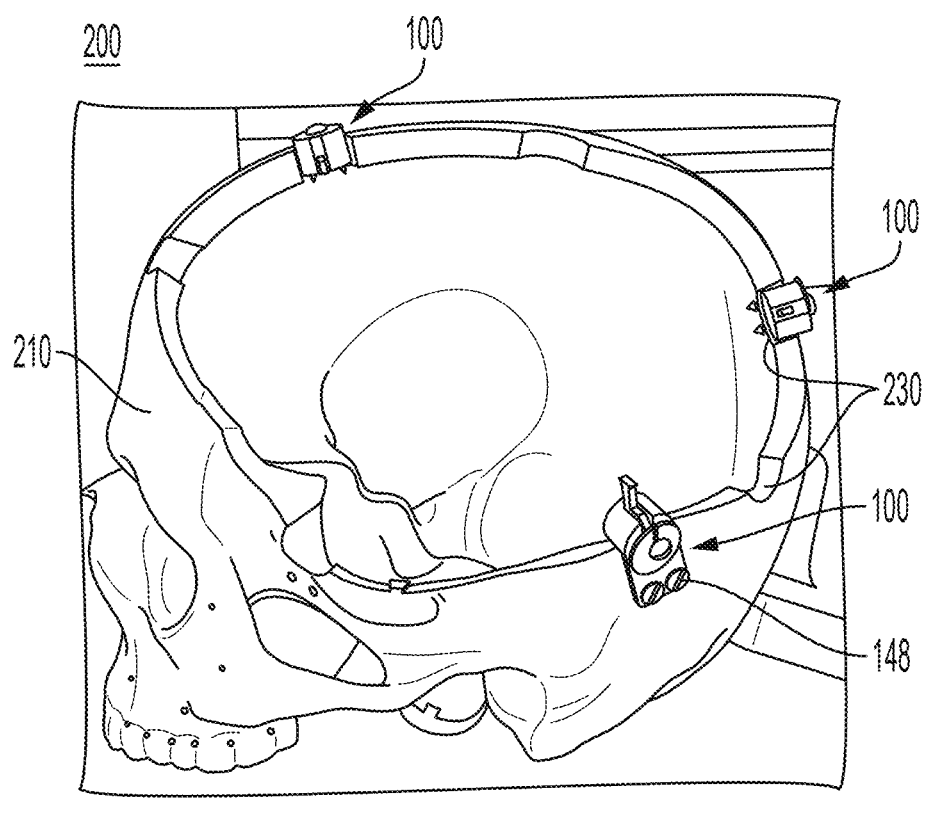
FIG. 8A-8B are isometric views of a system for adjustably fixing a first structure to a second structure according to some embodiments of the present technology.

As shown in FIGS. 1A-3, the device 100 includes a mounting bracket 140 that is connected to the first axial end 110A of the body 110 at a second side 116 that is opposite the slot 130. The mounting bracket 140 has a proximal end 142 that is connected to the first axial end 110A of the body and a distal end 144 that extends laterally outward from the second side 116 of the body 110. The distal end 144 is configured to be mounted to a first structure, such as the skull of a craniectomy patient. In some embodiments, the distal end 144 includes at least one mounting hole 146 that is configured to receive a fastener 148 (e.g., self-tapping-bone screw, bolt, etc.) for mounting the device 100 to the first structure, as shown in FIG. 8A. In some embodiments, the device 100 is mounted to the first structure via an adhesive on a bottom surface of the distal end 144. In some embodiments, the mounting bracket 140 is formed of a malleable material such that the distal end 144 is configured to conform to the contour of the first structure. In some embodiments, the mounting bracket 140 is formed of a metal material, such a titanium alloy (e.g., Ti-6AL-4V Grade 5 titanium alloy).

As shown in FIG. 1B, the device 100 includes a support member 150 that is retained in the bore 120 and is configured to move longitudinally in the bore 120. The support member 150 has a base 152 that is configured to be retained in the bore 120, and an arm 154 that extends from a first side 153 of the base 152 through the slot 130 such that the arm protrudes outward from the first side 112 of the body 110. The arm 154 is configured to support a second structure a longitudinal distance from the first structure (i.e., the second structure is supported a distance above, below, or flush with the first structure as measured along the longitudinal axis L). In some embodiments, the first structure is the skull of a craniectomy patient, and the second structure is a bone flap that was temporarily removed from the skull during the craniectomy. In some embodiments, the first structure is the skull of a craniectomy patient, and the second structure is a protective covering (e.g., a titanium meshing) positioned over an opening in the skull resulting from the craniectomy. In some embodiments, the support member 150 is formed of a metal material, such a titanium alloy (e.g., Ti-6AL-4V Grade 5 titanium alloy).

Figure 4:
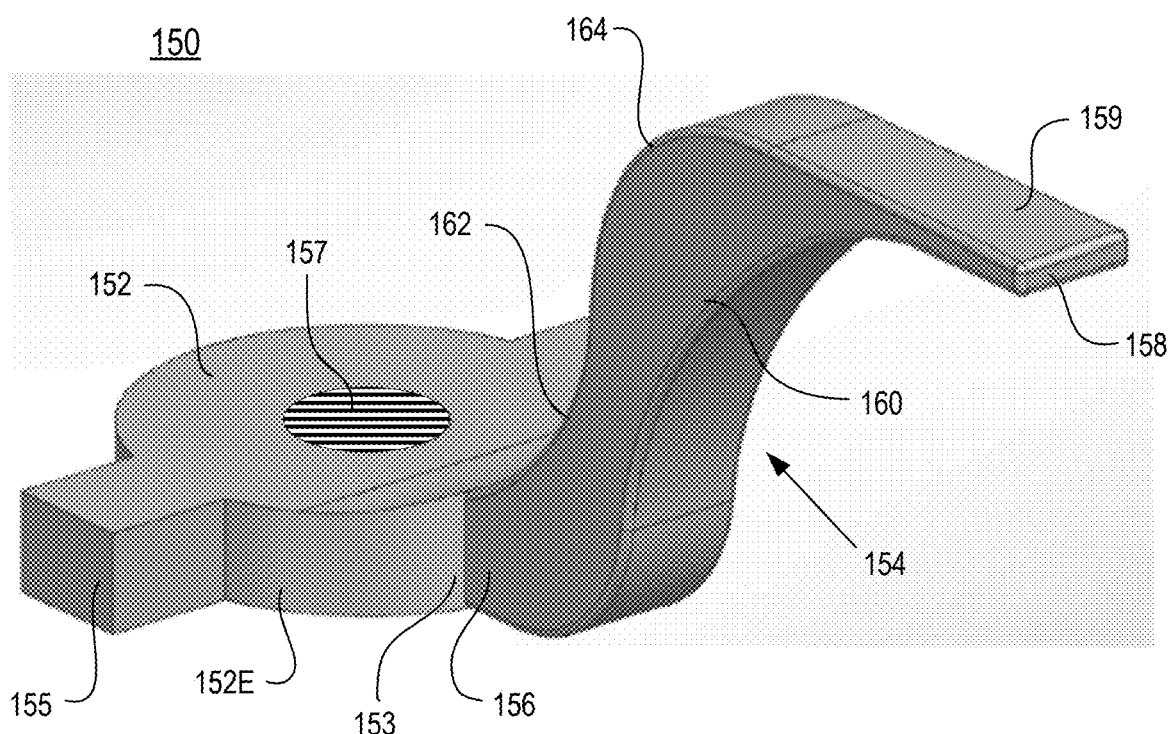
FIG. 4 is an isometric view of a support member of the cranial fixation device of FIG. 1.
Figure 5:
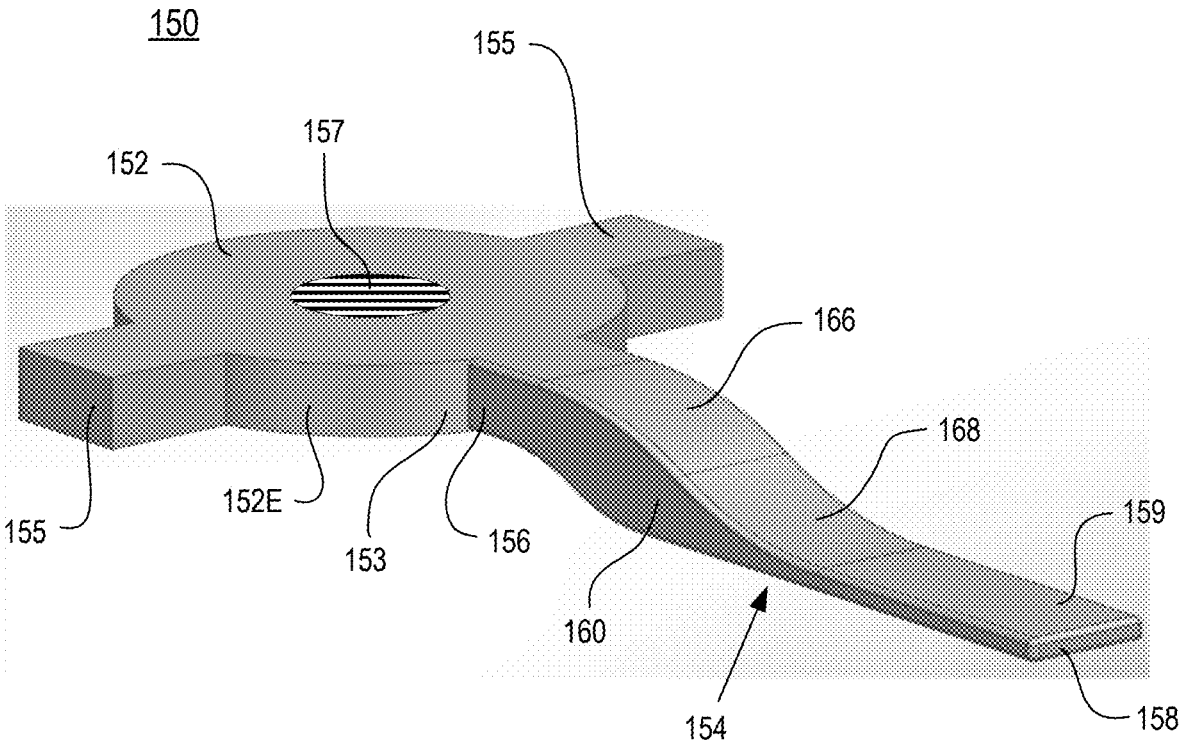
FIG. 5 is an isometric view of a support member of the cranial fixation device of FIG. 2.

As shown in FIGS. 4-5, the arm 154 of the support member 150 has a proximal end 156 that is connected to the first side 112 of the body 110, a distal end 158 that has a support surface 159 that is configured to support the second structure, and an intermediate section 160 that connects the proximal end 156 and the distal end 158. The intermediate section 160 is curved such that the proximal end 156 and the distal end 158 are at different positions as measured along the longitudinal axis L. In some embodiments, the intermediate section 160 has an upper concave curved portion 162 adjacent to the proximal end 156 and an upper convex curved portion 164 adjacent to the distal end 158 such that the distal end 158 is positioned above the proximal end 156 as measured along the longitudinal axis L, as shown in FIGS. 1A, 1B, and 4. In such embodiments, the first structure is the skull of a craniectomy patient, and the second structure is a protective covering (e.g., a titanium meshing) positioned over an opening in the skull resulting from the craniectomy. In some embodiments, the intermediate section 160 has an upper convex curved portion 166 adjacent to the proximal end 156 and an upper concave curved portion 168 adjacent to the distal end 158 such that the distal end 158 is positioned below the proximal end 156 as measured along the longitudinal axis L, as shown in FIGS. 2 and 5. In such embodiments, the first structure is the skull of a craniectomy patient, and the second structure is a bone flap that was temporarily removed from the skull during the craniectomy. However, the present technology is not limited thereto and contemplates embodiments where the intermediate section 160 has any number of curved portions in any arrangement to determine the longitudinal positioning of the distal end 158 and the proximal end 156.

In some embodiments, at least one tab 155 protrudes outward from an exterior surface 152E of the base 152 of the support member 150, as shown in FIGS. 4-5. The tab 155 corresponds in shape to, and is configured to be retained in, the groove 122 of the bore 120 to retain the support member 150 in the bore 120 and resist twisting and lateral movements of the support member 150 in the bore 120. The base 150 corresponds in shape to the bore 120 such that the exterior surface 152E of the base 150 abuts the interior wall 124 that defines the bore 120 in the body 110. In some embodiments, the base 152 includes two opposing tabs 155 that are each generally perpendicular to the arm 154. However, the present technology is not limited thereto and contemplates embodiments where the base 152 includes any number of tabs 155 in any arrangement. In some embodiments, the base 152 has a generally cylindrical shape such that the tabs 155 and the arm 154 extend radially outward therefrom. However, the present technology is not limited thereto and contemplates embodiments where the base 152 is differently shaped.

Figure 6:
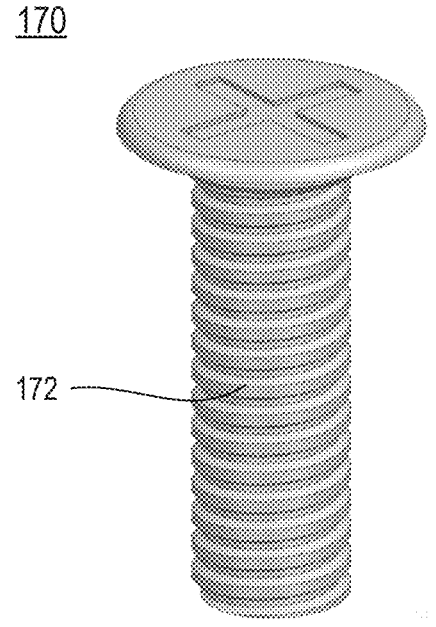
FIG. 6 is an isometric view of a lead screw of a cranial fixation device according to some embodiments of the present technology.
Figure 7:
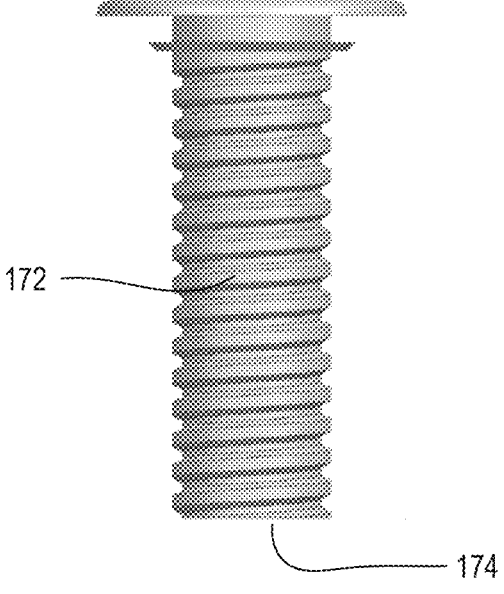
FIG. 7 is an elevational view of the lead screw of FIG. 6.

The base 152 has a threaded hole 157 passing therethrough, as shown in FIGS. 4-5, that is configured to receive a lead screw 170 for longitudinally positioning the support member 150 in the bore 120, as shown in FIG. 1B. As shown in FIGS. 6-7, the lead screw 170 has a threaded exterior surface 172 that is configured to engage the threaded hole 157 such that rotation of the lead screw 170 moves the support member 150 longitudinally in the bore 120. Thus, rotation of the lead screw 170 adjusts the longitudinal distance between the first structure and the second structure. For example, in some embodiments where the first structure is the skull of a craniectomy patient and the second structure is a bone flap removed from the skull during the craniectomy or a protective covering positioned over a hole in the skull resulting from the craniectomy, the lead screw 170 is initially rotated such that the support member 150 is retained at an uppermost position in the bore 120 to account for the patient's brain being swollen following the craniectomy, and the lead screw is rotated at predetermined intervals (e.g., based on periodic monitoring of the swelling of the patient's brain) to incrementally reduce the longitudinal distance between the first structure and the second structure as the swelling of the patient's brain reduces. Thus, the lead screw 170 allows the bone flap or protective covering to be held in a raised position to accommodate herniation in the patient's brain and allows the bone flap or protective covering to be incrementally lowered over time as the patient's ICP decreases. In some embodiments, the lead screw 170 has a flat bottom face 174, as shown in FIG. 7, that is configured to be retained in a corresponding depression in a bottom surface defining the bore 120 (not shown) to hold the lead screw 170 in an appropriate position.

In some embodiments, the device 100 includes a cap 180 that is connected to the first axial end 110A of the body 110, as shown in FIGS. 1A-2. The cap 180 is configured to at least partially seal the first axial end 110A of the body 110 to protect the internal components of the device 100, such as the threaded exterior surface 172 of the lead screw 170 and the threaded hole 157 of the support member 150, from in vivo conditions. The cap 180 has a notch 182 that extends laterally from an edge 184 to a center 186 of the cap 180. The notch 182 is configured to receive the lead screw 170 thereby securing the cap 180 to the body 110 and providing additional rigidity to prevent lateral and longitudinal movement of the lead screw 170 within the bore 120. In some embodiments, the cap 180 is formed of a metal material, such a titanium alloy (e.g., Ti-6AL-4V Grade 5 titanium alloy).

Figure 8B:
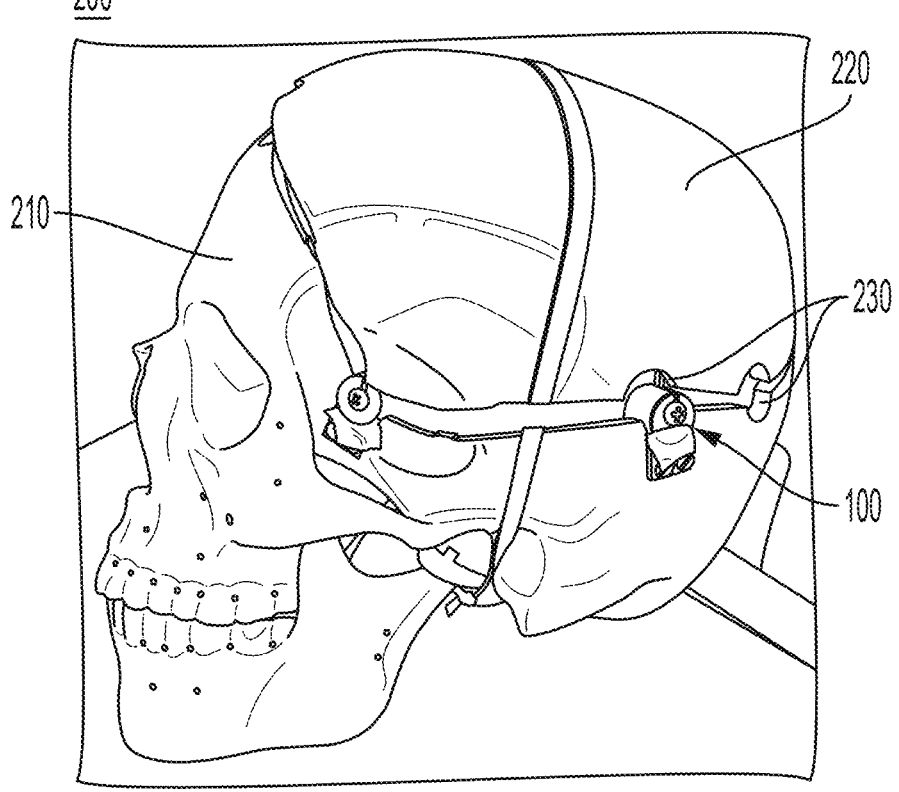

As shown in FIGS. 8A-8B, a system for adjustably fixing a first structure to a second structure is generally designated by the numeral 200. The system 200 includes a first structure 210, a second structure 220, and at least one burr hole 230 separating the first structure 210 and the second structure

220. In some embodiments, the first structure 210 is the skull of a craniectomy patient, and the second structure 220 is a bone flap that was temporarily removed from the skull during the craniectomy. In some embodiments, the first structure 210 is the skull of a craniectomy patient, and the second structure 220 is a protective covering (e.g., a titanium meshing) positioned over an opening in the skull resulting from the craniectomy. The system 200 includes at least one cranial fixation device 100 as described above. Each cranial fixation device 100 is positioned within a corresponding burr hole 230 such that the arms 154 of the cranial fixation devices 100 support the second structure 220 at a desired longitudinal distance from the first structure 210. As the swelling of the patient's brain reduces over time, the lead screws 170 of the cranial fixation devices 100 are rotated at predetermined intervals to incrementally reduce the longitudinal distance between the first structure 210 and the second structure 220. In the embodiment shown in FIG. 8A, the system 200 includes three cranial fixation devices 100. However, the present technology is not limited thereto and contemplates embodiments where the first structure 210 and the second structure 220 are separated by any number of burr holes such that the system 200 includes any number of cranial fixation devices 100.

As shown in FIG. 9, a method for adjustably fixing a first structure to a second structure is generally designated by the numeral 300. At 310, the method 300 includes providing a cranial fixation device 100, as described above. At 320, the method 300 includes positioning the body 110 of the cranial fixation device 100 adjacent to an edge of the first structure such that the distal end 144 of the mounting bracket 140 is atop the first structure. In some embodiments, at 330 the method 300 includes conforming the mounting bracket 140 to the contour of the first structure. At 340, the method 300 includes inserting a fastener 148 through each of the at least one mounting holes 146 of the mounting bracket 140 to secure the cranial fixation device 100 to the first structure. At 350, the method 300 includes positioning a bottom surface of the second structure atop the arm 154 of the support member 150 of the cranial fixation device 100. At 360, the method 300 includes rotating the lead screw 170 to adjust a longitudinal distance between the first structure and the second structure. At 370, the method 300 includes rotating the lead screw 170 at predetermined intervals to incrementally reduce the longitudinal distance between the first structure and the second structure.

As will be apparent to those skilled in the art, various modifications, adaptations, and variations of the foregoing specific disclosure can be made without departing from the scope of the technology claimed herein. The various features and elements of the technology described herein may be combined in a manner different than the specific examples described or claimed herein without departing from the scope of the technology. In other words, any element or feature may be combined with any other element or feature in different embodiments, unless there is an obvious or inherent incompatibility between the two, or it is specifically excluded.

References in the specification to "one embodiment," "an embodiment," etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described.

The singular forms "a," "an," and "the" include plural reference unless the context clearly dictates otherwise. Thus, for example, a reference to "a plant" includes a plurality of such plants. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition, or step being referred to is an optional (not required) feature of the technology. The term "and/or" means any one of the items, any combination of the items, or all of the items with which this term is associated.

Each numerical or measured value in this specification is modified by the term "about." The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents of carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third, and upper third, etc.

As will also be understood by one skilled in the art, all language such as "up to," "at least," "greater than," "less than," "more than," "or more," and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

What is claimed is:

1. A fixation device comprising:
   a body having a first axial end and a second axial end defining a longitudinal axis of the fixation device, the body having a bore therein extending longitudinally from the first axial end toward the second axial end and a slot in a first side of the body, the slot extending longitudinally from the first axial end toward the second axial end and laterally from the first side of the body to the bore;
   a mounting bracket connected to the first axial end of the body at a second side opposite the slot, the mounting bracket having a proximal end connected to the first axial end of the body and a distal end extending outward from the second side of the body, the distal end configured to be mounted to a first structure;

a support member retained in the bore and configured to move longitudinally in the bore, the support member having a base retained in the bore and an arm extending from a first side of the base through the slot such that the arm protrudes outward from the first side of the body, the arm configured to support a second structure a longitudinal distance from the first structure; and a lead screw configured to engage a threaded hole in the base of the support member to retain the support member in the bore whereby rotation of the lead screw moves the support member longitudinally in the bore to adjust the longitudinal distance of the second structure from the first structure.

2. The fixation device of claim 1, wherein the arm of the support member comprises a proximal end connected to the first side of the base, a distal end having a support surface configured to support the second structure, and an intermediate section connecting the proximal end and the distal end, the intermediate section having at least one curved portion such that the proximal end and the distal end are at different positions along the longitudinal axis.

3. The fixation device of claim 2, wherein the intermediate section comprises an upper concave curved portion adjacent the proximal end and an upper convex curved portion adjacent the distal end such that the distal end is positioned above the proximal end along the longitudinal axis.

4. The fixation device of claim 2, wherein the intermediate section comprises an upper convex curved portion adjacent the proximal end and an upper concave curved portion adjacent the distal end such that the distal end is positioned below the proximal end along the longitudinal axis.

5. The fixation device of claim 1, wherein the bore further comprises at least one longitudinal groove configured to retain a tab of the base of the support member.

6. The fixation device of claim 1, further comprising a cap connected to the first axial end of the body, the cap having a lateral notch configured to receive the lead screw.

7. The fixation device of claim 1, wherein the body has a generally cylindrical shape and is configured to be received in a burr hole separating the first structure and the second structure.

8. The fixation device of claim 7, wherein the first structure is a skull and the second structure is a bone flap removed from the skull or a protective covering positioned over an opening in the skull.

9. The fixation device of claim 1, wherein the mounting bracket is configured to conform to a contour of the first structure.

10. The fixation device of claim 1, wherein the distal end of the mounting bracket comprises at least one mounting hole configured to receive a fastener for mounting the fixation device to the first structure.

11. A method of adjustably fixing a first structure to a second structure, the method comprising:

providing a fixation device comprising:

a body having a first axial end and a second axial end defining a longitudinal axis of the fixation device, the body having a bore therein extending longitudinally from the first axial end toward the second axial end and a slot in a first side of the body, the slot extending longitudinally from the first axial end toward the second axial end and laterally from the first side of the body to the bore;

a mounting bracket connected to the first axial end of the body at a second side opposite the slot, the mounting bracket having a proximal end connected to the first axial end of the body and a distal end extending outward from the second side of the body, the distal end having at least one mounting hole therein;

a support member retained in the bore and configured to move longitudinally in the bore, the support member having a base retained in the bore and an arm extending from a first side of the base through the slot such that the arm protrudes outward from the first side of the body; and a lead screw configured to engage a threaded hole in the base of the support member to retain the support member in the bore whereby rotation of the lead screw moves the support member longitudinally in the bore;

positioning the body of the fixation device adjacent an edge of the first structure such that the distal end of the mounting bracket is atop the first structure;

inserting a fastener through each of the at least one mounting holes of the mounting bracket to secure the fixation device to the first structure;

positioning a bottom surface of the second structure atop the arm of the support member; and rotating the lead screw to adjust a longitudinal distance between the first structure and the second structure.

12. The method of claim 11, wherein the arm of the support member comprises a proximal end connected to the first side of the base, a distal end having a support surface configured to support the second structure, and an intermediate section connecting the proximal end and the distal end, the intermediate section having at least one curved portion such that the proximal end and the distal end are at different positions along the longitudinal axis.

13. The method of claim 12, wherein the intermediate section comprises an upper concave curved portion adjacent the proximal end and an upper convex curved portion adjacent the distal end such that the distal end is positioned above the proximal end along the longitudinal axis.

14. The method of claim 12, wherein the intermediate section comprises an upper convex curved portion adjacent the proximal end and an upper concave curved portion adjacent the distal end such that the distal end is positioned below the proximal end along the longitudinal axis.

15. The method of claim 11, wherein the bore further comprises at least one longitudinal groove configured to retain a tab of the base of the support member.

16. The method of claim 11, wherein the fixation device further comprises a cap connected to the first axial end of the body, the cap having a lateral notch configured to receive the lead screw.

17. The method of claim 11, wherein the body has a generally cylindrical shape and is configured to be received in a burr hole separating the first structure and the second structure.

18. The method of claim 17, wherein the first structure is a skull and the second structure is a bone flap removed from the skull or a protective covering positioned over an opening in the skull.

19. The method of claim 11, further comprising conforming the mounting bracket to a contour of the first structure.

20. The method of claim 11, further comprising rotating, at predetermined intervals, the lead screw to incrementally reduce the longitudinal distance between the first structure and the second structure.

* * * * *